(12) United States Patent
Kim et al.

(10) Patent No.: US 7,754,452 B2
(45) Date of Patent: Jul. 13, 2010

(54) POLYMERASE CHAIN REACTION MODULE, AND MULTIPLE POLYMERASE CHAIN REACTION SYSTEM INCLUDING THE MODULE

(75) Inventors: Jin-tae Kim, Hwaseong-si (KR); Kak Namkoong, Seoul (KR); Kwang-wook Oh, Hwaseong-si (KR); Chin-sung Park, Yongin-si (KR); Yu-jin Seo, Daejeon-si (KR)

(73) Assignee: Samsung Electronics Co., Ltd. (KR)

( * ) Notice: Subject to any disclaimer, the term of this patent is extended or adjusted under 35 U.S.C. 154(b) by 312 days.

(21) Appl. No.: 11/377,793

(22) Filed: Mar. 16, 2006

(65) Prior Publication Data
US 2006/0246580 A1  Nov. 2, 2006

(30) Foreign Application Priority Data
May 2, 2005  (KR) ............... 10-2005-0036687

(51) Int. Cl.
*C12P 19/34* (2006.01)
*C12M 1/36* (2006.01)
*G01N 15/06* (2006.01)

(52) U.S. Cl. .......... 435/91.2; 435/283.1; 435/287.2; 435/288.7; 422/82.05; 422/82.08

(58) Field of Classification Search .......... None
See application file for complete search history.

(56) References Cited

U.S. PATENT DOCUMENTS

| 4,821,972 | A * | 4/1989 | Grollimund et al. ...... 242/523.1 |
| 6,818,185 | B1 * | 11/2004 | Petersen et al. ............. 422/102 |
| 7,172,897 | B2 * | 2/2007 | Blackburn et al. ........ 435/287.2 |
| 7,244,961 | B2 * | 7/2007 | Jovanovich et al. .......... 257/48 |
| 2005/0047973 | A1 * | 3/2005 | Schulz et al. ............... 422/104 |

FOREIGN PATENT DOCUMENTS

KR   1020050056870 A   6/2005

* cited by examiner

*Primary Examiner*—BJ Forman
(74) *Attorney, Agent, or Firm*—Cantor Colburn LLP

(57) ABSTRACT

Provided are a polymerase chain reaction (PCR) module and a PCR system including the same. The PCR module includes: a detachable PCR chip including a PCR chamber unit in which a PCR solution is accommodated; a heater unit for heating the PCR solution in the PCR chip with a preset temperature; a detecting unit for detecting a PCR signal of the PCR solution; a PCR chip installation unit for mounting/detaching the PCR chip using a one-touch method, in which the heater unit is adhered to the PCR chip with a predetermined pressure when mounting the PCR chip and the heater unit is separated from the PCR chip when detaching the PCR chip; and a housing covering at least the heater unit and the detecting unit so that they are not exposed to the outside.

25 Claims, 14 Drawing Sheets

POLYMERASE CHAIN REACTION MODULE, AND MULTIPLE POLYMERASE CHAIN REACTION SYSTEM INCLUDING THE MODULE

This application claims the priority of Korean Patent Application No. 10-2005-0036687, filed on May 2, 2005 in the Korean Intellectual Property Office, the disclosure of which is incorporated herein in its entirety by reference.

BACKGROUND OF THE INVENTION

1. Field of the Invention

The present invention relates to a polymerase chain reaction (PCR) module and a multiple PCR system having the PCR module, and more particularly, to a PCR module capable of preventing contamination of a detecting unit and a heater unit when installing or removing a PCR chip, and a multiple PCR system including the PCR module.

2. Description of the Related Art

Polymerase chain reaction (PCR), which is a technology to amplify DNA copies of specific DNA or RNA fragments in a reaction container, is an epoch-making development in life science technology. In the PCR technology at the beginning, PCR products are separated on a gel and the approximate amount of the PCR products is estimated. Recently, however, co-amplification of different samples at different temperatures has been carried out and precisely monitored in real-time.

FIG. 1 is a schematic block diagram of a multiple PCR system 1 disclosed in Korean Patent Application No. 10-2004-0102738 filed by the applicant of the present invention on Dec. 8, 2004. In the multiple PCR system 1, co-amplification of different samples at different temperatures is performed in addition to monitoring the PCR reaction process in real-time, as described above. Referring to FIG. 1, the multiple PCR system 1 includes a plurality of PCR modules 40 and a host computer 50, which controls the PCR modules 40 and collects data. Each of the PCR modules 40 performs a PCR reaction on a single sample at a specific temperature and monitors the process and transmits the monitoring results to the host computer 50 in real-time. Any number of PCR modules 40 can be detachably installed in the PCR system 1 and connected to the host computer 50.

50 in real-time. Any number of PCR modules 40 can be detachably installed in the PCR system 1 and connected to the host computer 50.

As illustrated in FIG. 1, each of the PCR modules 40 includes a detachable microchip-type PCR reaction container (hereinafter referred to as a PCR chip) 10, a detecting unit 30 that detects a PCR product signal based on the amount of a PCR product of a sample solution (hereinafter referred to as a PCR solution) contained in a PCR reaction chamber (hereinafter referred to as a PCR chamber) 11 of the PCR chip 10 in which a PCR reaction is to occur, and an operation control unit 41 that automatically controls the whole PCR process and transmits and receives data to and from the host computer 50. The detachable PCR chip 10 can be used once or repeatedly. The PCR chamber 11 in which the PCR solution is accommodated and where the PCR reaction occurs is formed in the PCR chip 10. The PCR module 40 further includes a heater 20 contacting the bottom surface of the PCR chip 10 and transmitting heat so that the temperature of the PCR chip 10 is maintained at an appropriate temperature. A separate power supply device 51 applies a constant voltage to the heater 20. In addition, the PCR module 40 may further include a cooling device 43 besides the heater 20 so that the temperature of the PCR solution inside the PCR chip 10 quickly reaches a target temperature.

The detecting unit 30 in the PCR module 40 includes a light source 31 or an AC power supply unit 33, and detects a PCR product signal based on the amount of a PCR product. The PCR product signal may be a fluorescent signal emitted from the PCR chamber 11 disposed inside the PCR chip 10. In this case, the detecting unit 30 includes the light source 31 which emits light onto the PCR solution. After the light is emitted from the light source 31 onto the PCR solution, a fluorescent light emitted from the PCR solution is detected by a detector (not shown). The PCR product signal can also be an electrical signal, in which case the detecting unit 30 includes a sensor (not shown) for detecting the electrical signal. The sensor installed inside the PCR chip 10 senses a PCR product signal generated when an AC current is supplied to the PCR solution and transmits the sensed PCR product signal to the host computer 50. To do this, the detecting unit 30 includes the AC power supply unit 33 instead of the light source 31.

The operation control unit 41, which transmits and receives data to and from the host computer 50 by automatically controlling the entire PCR process, includes a central processing unit (CPU) 42 composed of a microprocessor, an auxiliary memory device 44, and a random access memory (RAM) 45, and controls the PCR process according to a set program. The operation control unit 41 independently controls the detecting unit 30, the PCR chip 10, the heater 20, the cooling device 43, and the power supply device 51 via a data communication unit (not shown) in real-time. Also, the operation control unit 41 performs a predetermined operation according to the set program or predetermined parameter values set by a user after performing appropriate operations based on information obtained from the sensor adhered to the detecting unit 30, the PCR chip 10, the heater 20, and the cooling device 43 or the data communication unit. For example, according to the PCR process, the temperature of the PCR chamber 11 is appropriately controlled, or operation of the cooling device 43, the detecting intervals of the detecting unit 30, etc. can be controlled. In addition, the operation control unit 41 may further include a separate input and output device 46 so that the PCR module 40 can be independently driven.

FIG. 2 is a schematic perspective view of the multiple PCR system 1 illustrated in FIG. 1. As illustrated in FIG. 2, the multiple PCR system 1 has a space in which a plurality of modules 40 can be accommodated. A plurality of slots (not shown) are formed in the space in which the PCR modules 40 can be installed, and thus the PCR modules 40 are easily detachable. Also, a display unit 60 which displays data received from the PCR modules 40 and an input unit 70 in which the user inputs required signals are installed in the multiple PCR system 1.

FIG. 3 is a perspective view of one of the PCR modules 40. As illustrated in FIG. 3, the PCR module 40 includes a main body 48 and a cover 47 installed on the main body 48 capable of performing a hinge motion. A pin 49 in which a plurality of electrodes are formed is formed on the bottom surface of the main body 48. The PCR module 40 can be installed in the slot in the PCR system 1 via the pin 49. When the PCR module 40 uses, for example, a fluorescent signal as the PCR product signal, a detecting unit 30 composed of an optical system including a light source having lenses is installed in the cover 47. Also, a space for accommodating the PCR chip 10 is formed in a portion of the main body 48 corresponding to the detecting unit 30, and the heater 20 is installed below the space. In such a structure, if the cover 47 closes by rotating the cover 47 after the PCR chip is placed in the space above the heater 20, the detecting unit 30 of the cover 47 faces the PCR chamber 11 of the PCR chip 10, and thus, the fluorescent signal emitted from the PCR solution within the PCR chamber 11 can be detected. As illustrated in FIG. 4, the PCR chamber 11 in which the PCR solution is accommodated is formed in the PCR chip 10, the PCR solution flowing in via an inlet 12 and flowing out via an outlet 13. Thus, the detecting unit 30 can detect the fluorescent signal emitted from the PCR solution during the PCR reaction.

However, in the PCR module 40 having the above-described structure, the optical system in the detecting unit 30 is exposed to the outside when mounting the PCR chip 10 in the PCR module 40, and thus the detecting unit 30 is susceptible to contamination. As a result, the accuracy of measured values is reduced. The heater 20 also gets contaminated when installing the PCR chip 10, thereby making it difficult to appropriately adjust the temperature of the PCR solution inside the PCR chip 10. In addition, because the user places the PCR chip 10 on top of the heater 20, the heater 20 and the PCR chip 10 can get damaged due to carelessness and it is difficult to adhere the heater 20 and the PCR chip 10 with the optimum pressure. Furthermore, it is inconvenient for the user to use since the cover 47 of the PCR module 40 needs to be opened and closed whenever installing or removing the PCR chip 10.

SUMMARY OF THE INVENTION

The present invention provides a polymerase chain reaction (PCR) module capable of preventing contamination of a detecting unit and a heater unit when installing or removing a PCR chip, and a multiple PCR system including the PCR module.

The present invention also provides a PCR module that is easily mountable or detachable with one touch, and a multiple PCR system including the PCR module.

The present invention also provides a PCR module that is structured so that a heater and the PCR chip can be optimally adhered to each other, and a multiple PCR system including the PCR module.

According to an aspect of the present invention, there is provided a PCR module, including: a detachable PCR chip including a PCR chamber unit in which a PCR solution is accommodated; a heater unit for heating the PCR solution in the PCR chip with a preset temperature; a detecting unit for detecting a PCR signal of the PCR solution; a PCR chip installation unit for mounting/detaching the PCR chip using a one-touch method, in which the heater unit is adhered to the PCR chip with a predetermined pressure when mounting the PCR chip and the heater unit is separated from the PCR chip when detaching the PCR chip; and a housing covering at least the heater unit and the detecting unit so that they are not exposed to the outside.

The PCR chip installation unit may include: a heater mounting guide for adhering the heater unit to the PCR chip with a predetermined pressure when mounting the PCR chip; a push rod which enables the PCR chip to be mounted by locking the heater mounting guide when the PCR chip is not yet mounted, and enables the heater mounting guide to adhere the heater unit to the PCR chip by releasing the heater mounting guide when mounting the PCR chip; and a detaching button to draw back the heater unit to separate the heater unit from the PCR chip when detaching the PCR chip. The heater mounting guide may have a link structure in which respective ends of the heater mounting guide are rotatably coupled to the heater unit and the housing.

The heater unit may be elastically biased towards the PCR chip by a spring.

The push rod may be elastically biased towards the heater mounting guide by a spring, and a first end of the push rod may push and lock the heater mounting guide when the PCR chip is not yet mounted. The first end of the push rod locking the heater mounting guide may be slanted, and the slanted surface may push the heater mounting guide when the PCR chip is not yet mounted. Also, a protrusion may be formed on a side of the push rod so that the protrusion can contact the bottom of the PCR chip when the PCR chip is being mounted. When mounting the PCR chip, the bottom of the PCR chip may be hooked by the protrusion of the push rod and the push rod may retreat from the heater mounting guide, thereby releasing the locked heater mounting guide.

The PCR chip installation unit further include an installation detecting sensor for detecting whether or not the PCR chip is mounted. For example, the installation detecting sensor may be a switch that is turned "on" by being pushed by a second end of the push rod when mounting the PCR chip and is turned "off" when the PCR chip is detached.

The PCR chip installation unit may further include: a cover encompassing the heater unit and the heater mounting guide to provide a safe movement path for the PCR chip when mounting or detaching the PCR chip and to protect the PCR chip; and a flat chip guide disposed between the cover and the heater unit to form the movement path for the PCR chip together with the cover. A curved protrusion corresponding to the width and height of the PCR chip may be formed in the center of the cover. In this case, the PCR chip may move between the curved protrusion of the cover and the chip guide. An aperture is formed in the chip guide so that the PCR chip disposed at the front of the chip guide and the heater unit disposed at the rear of the chip guide can adhere to each other when mounting the PCR chip.

Also, a window may be formed in a part of the cover facing the PCR chamber unit of the PCR chip mounted inside the PCR module. Then, light emitted from the detecting unit is incident on the PCR solution in the PCR chamber unit via the window, and fluorescent signals generated from the PCR solution may be transmitted to the detecting unit via the window.

The heater unit may include: a heater plate for heating the PCR chip by directly contacting the PCR chip; a substrate in which a circuit for setting a temperature of the heater plate to a preset temperature is installed; a substrate holder for fixing the substrate; and electrodes formed between the substrate and the heater plate to transmit current from the substrate to the heater plate. Also, the heater unit may further include a heater plate guide for fixing the electrodes and the heater plate together by encompassing the circumference of the electrodes and a top surface of the heater plate. The electrodes may prevent poor connection by being elastically biased towards the heater plate via a spring, and ends of the electrodes contacting the heater plate being flat. Also, a shaft is formed in a protrusion on both sides of the substrate holder so that the heater mounting guide can be rotatably coupled.

According to another aspect of the present invention, there is provided a PCR system including: the PCR module described above; and a host computer which controls the PCR module and collects data. Any number of PCR modules can be detachably installed. The PCR system can simultaneously cause PCR reaction to different PCR solutions at different temperatures using multiple PCR modules in addition to monitoring multiple PCR reaction processes in real-time via the host computer. Also, the PCR system may further include a plurality of slots for mounting at least one PCR module, and a pin in which electrodes are formed protrudes from a bottom of each of the PCR modules so that the PCR modules can be mounted in the slots.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
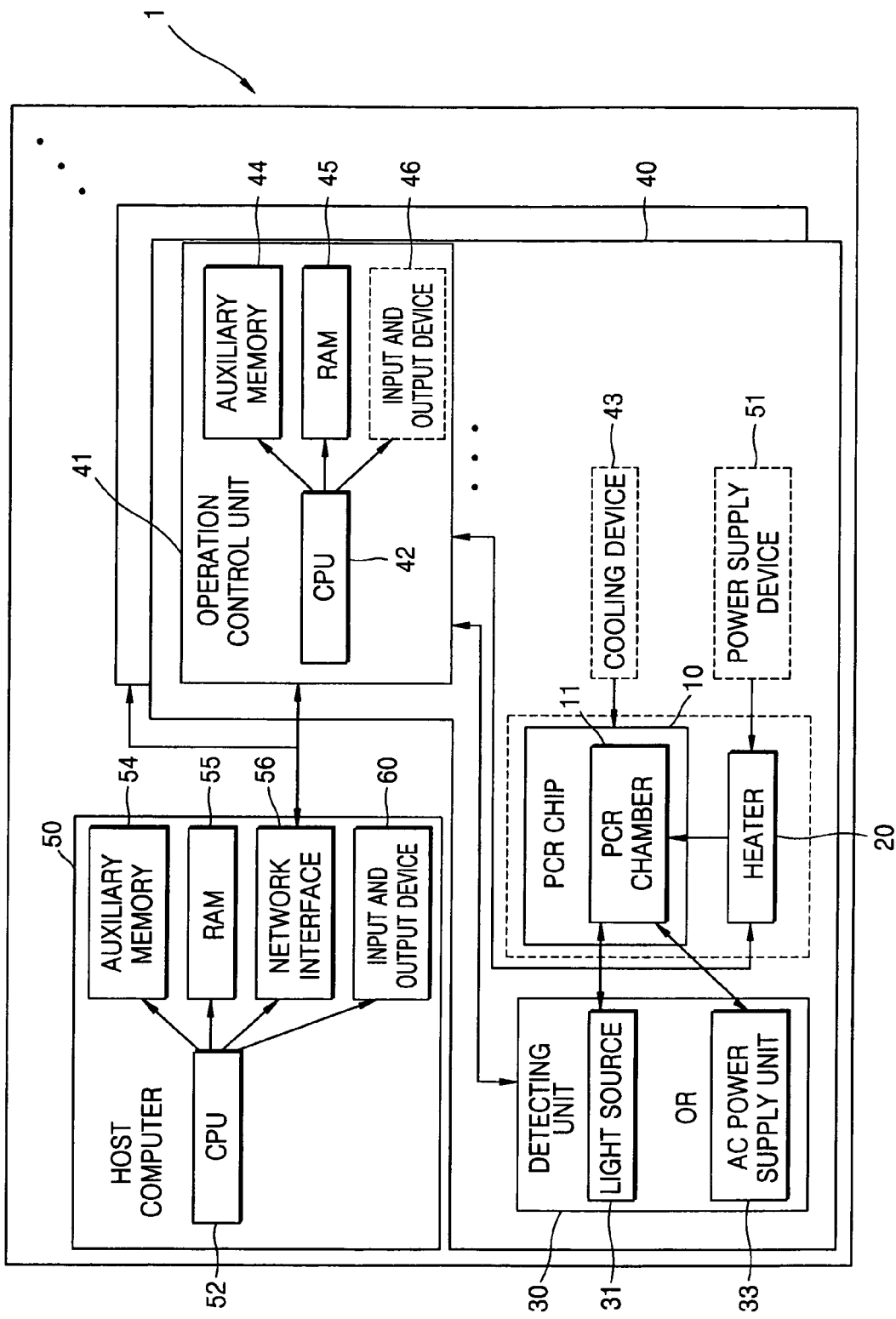
FIG. 1 is a schematic block diagram of a prior multiple polymerase chain reaction (PCR) system.
Figure 5A:
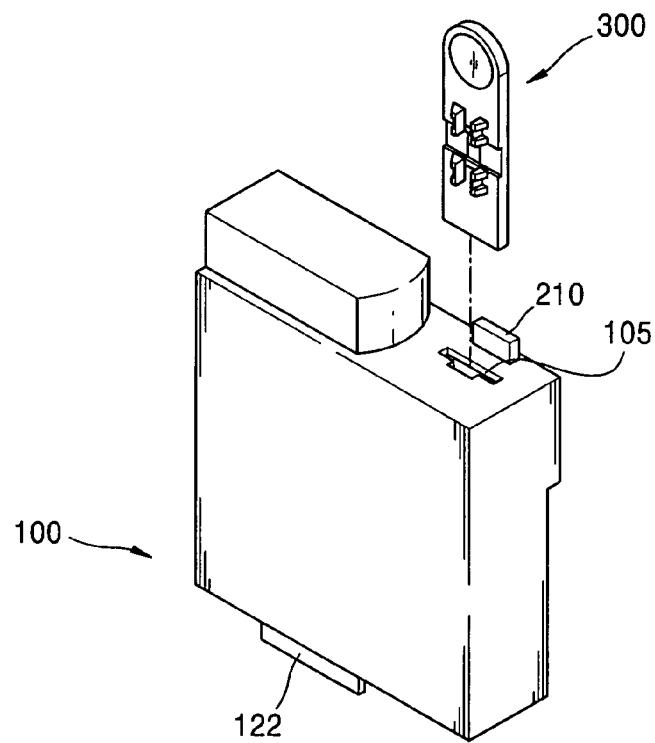
FIGS. 5A and 5B are perspective views of a PCR module according to an embodiment of the present invention.
Figure 5B:
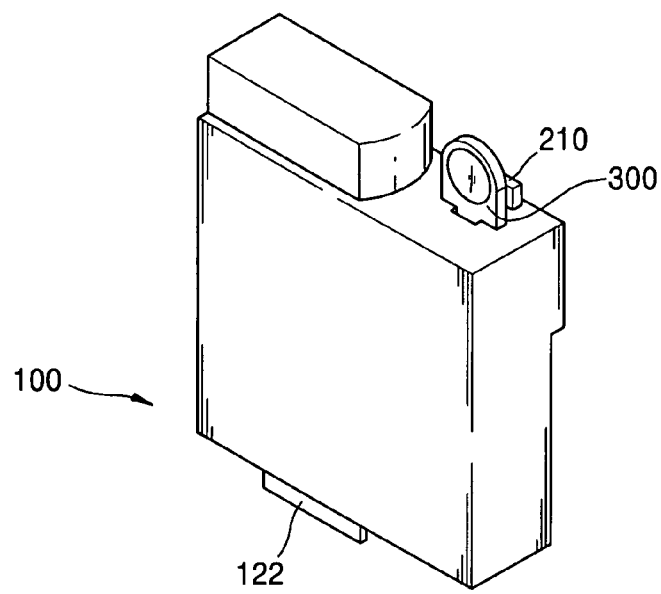

FIGS. 5A and 5B are perspective views of a PCR module 100 according to an embodiment of the present invention. Referring to FIG. 5A, both a detecting unit 110 (see FIG. 6) and a heater unit 230 (see FIG. 8B) are installed inside the PCR module 100 unlike a prior PCR module. Also, a PCR chip 300 can be installed with a single touch via an inserting slot 105 formed on top of the PCR module 100. Therefore, there is less possibility of a user causing damage when installing the PCR chip 100 because the detecting unit 110 and the heater unit 230 are not exposed to the outside. FIG. 5B is a view of the PCR module 100 in which the PCR chip 300 is installed. The PCR chip 300 can be detached from the PCR module 100 when a detaching button 210 is pressed. Therefore, the present invention contains improvement to parts of a prior PCR system 1 illustrated in FIG. 1 indicated by dotted-lined rectangles.

Figure 6:
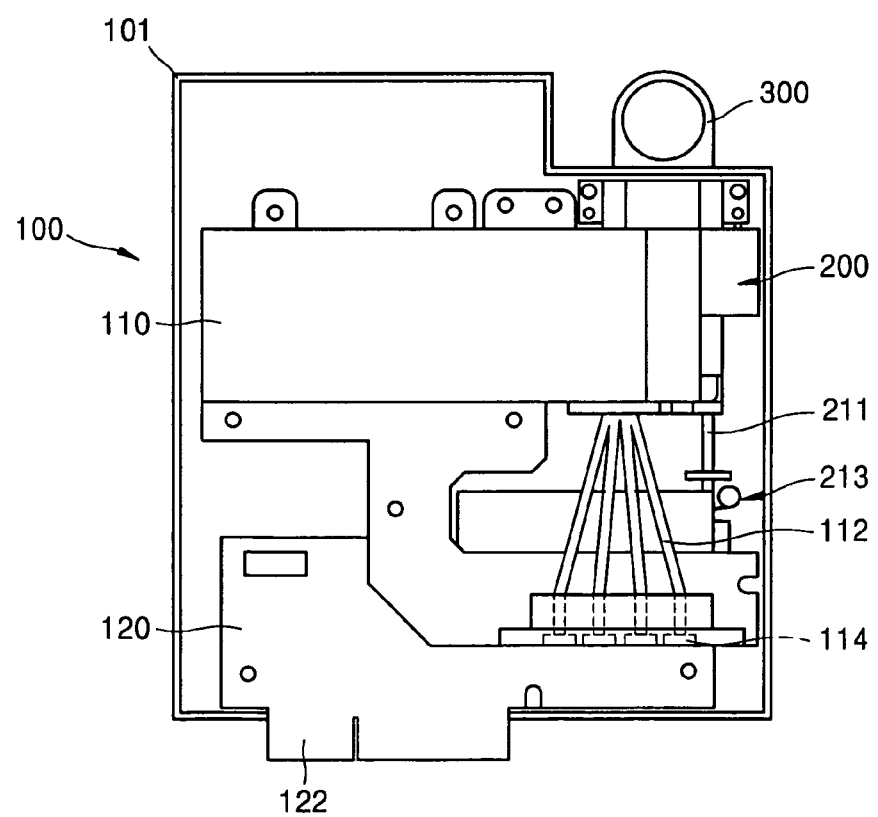
FIG. 6 is a diagram illustrating the inner structure of the PCR module illustrated in FIGS. 5A and 5B.

FIG. 6 is a diagram illustrating the inner structure of the PCR module 100 illustrated in FIGS. 5A and 5B. As illustrated in FIG. 6, the detecting unit 110, an operation control unit 120, and a PCR chip installation unit 200 are installed inside a housing 101 of the PCR module 100. The operation control unit 120 has the same function and structure as an operation control unit 41 of the prior PCR system 1. That is, the operation control unit 120 has a structure in which a central processing unit (CPU), an auxiliary device, etc. are mounted on a PCB circuit, and controls the PCR process according to a set program. In addition, a pin 122 in which electrodes are formed protrudes downwards from the housing 101 so that the PCR module 100 can be installed in a slot formed in a PCR system.

The detecting unit 110 illustrated as an example in FIG. 6 uses a fluorescent signal emitted from a PCR solution inside a PCR chamber (see FIG. 12) as a PCR product signal. Therefore, although not illustrated in FIG. 6, the detecting unit 110 includes a light source disposed to face the PCR chamber inside the PCR chip 300 and an optical system which condenses the fluorescent signal. The fluorescent signal is, for example, transmitted to a plurality of optical detectors 114 via a light transmitting element 112. The optical detectors 114 may be photodiodes, photo multiplier tubes (PMT), charge coupled devices (CCDs), etc. The optical detectors 114 measure the size of the fluorescent signal and transmit the result to the operation control unit 120. Thereafter, the operation control unit 120 analyzes the PCR reaction of the PCR solution based on the size of the fluorescent signal and transmits the results to the PCR system. Similar to the prior PCR system 1, the PCR signal may be an electrical signal in which case the detecting unit 110 includes sensors (not shown) to detect the electrical signal instead of the optical detectors 114 and includes an AC power supply unit instead of the light source.

Figure 7:
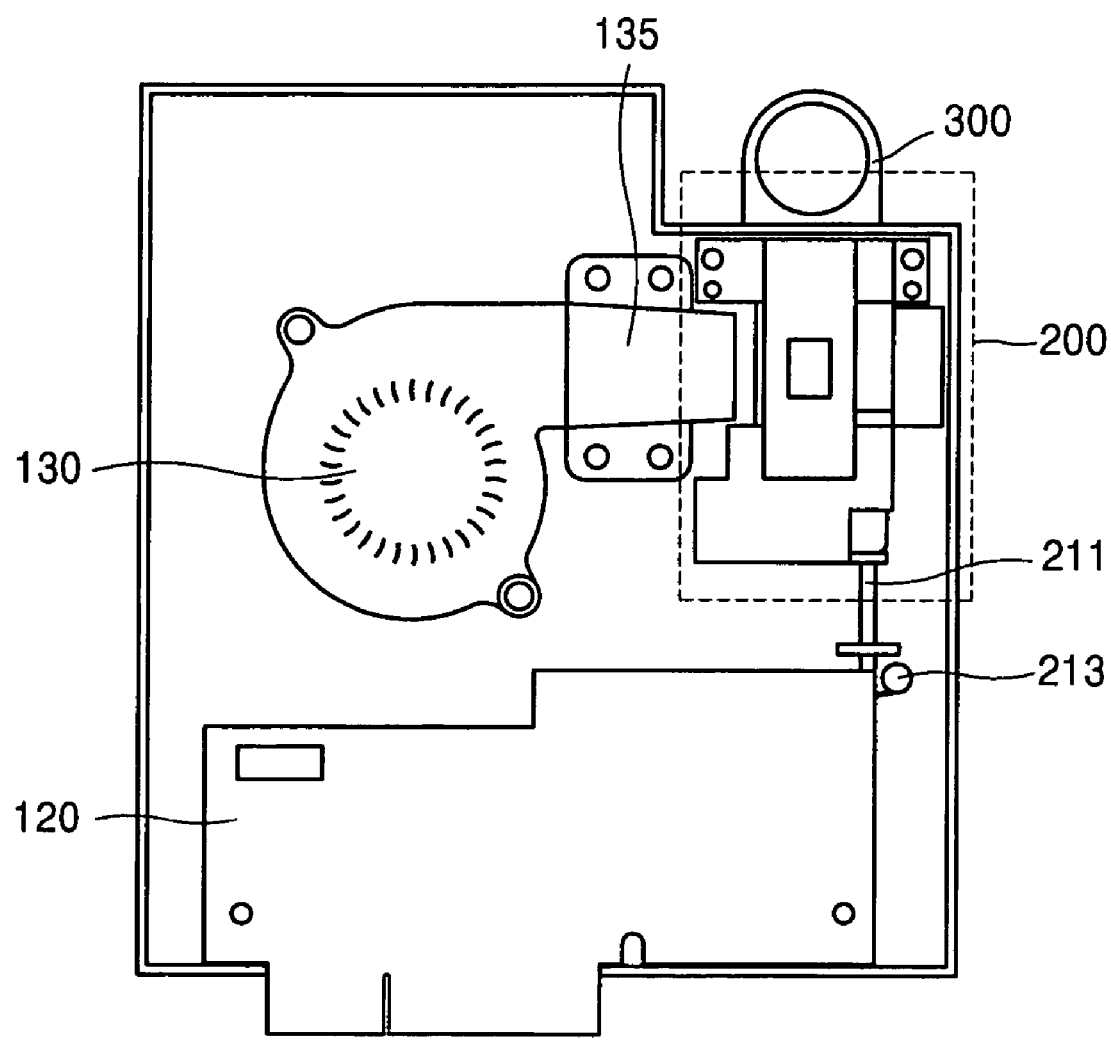
FIG. 7 is a diagram illustrating the inner structure of the PCR module illustrated in FIG. 6 from which a detecting unit is removed.

FIG. 7 is a diagram illustrating the inner structure of the PCR module 100 from which the detecting unit 110 is removed, including a cooling fan 130, a blast pipe 135, and the PCR chip installation unit 200. The purpose of the cooling fan 130 and the blast pipe 135 is to enable the temperature of the PCR solution inside the PCR chip 300 to quickly reach a target temperature as in the prior art. The PCR chip installation unit 200 enables the PCR chip 300 to be safely installed and removed from the PCR module 100, and applies the PCR chip 300 installed inside the PCR module 100 to the heater unit 230 with a pressure of, for example, about 20-30 psi. The PCR chip 300 can be installed and/or removed from the PCR module 100 without exposing the detecting unit 110 and the heater unit 230 to the outside by using the PCR chip installation unit 200 according to the current embodiment of the present invention.

Figure 8A:
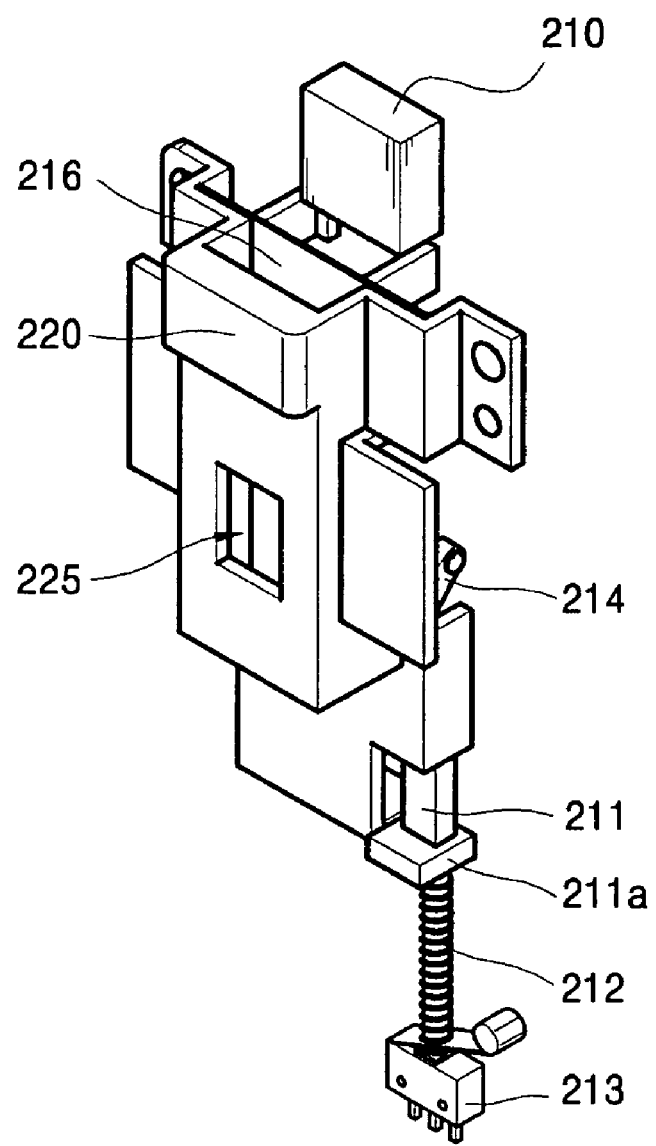
FIGS. 8A and 8B are exemplary views of a PCR chip installation unit according to an embodiment of the present invention.
Figure 8B:
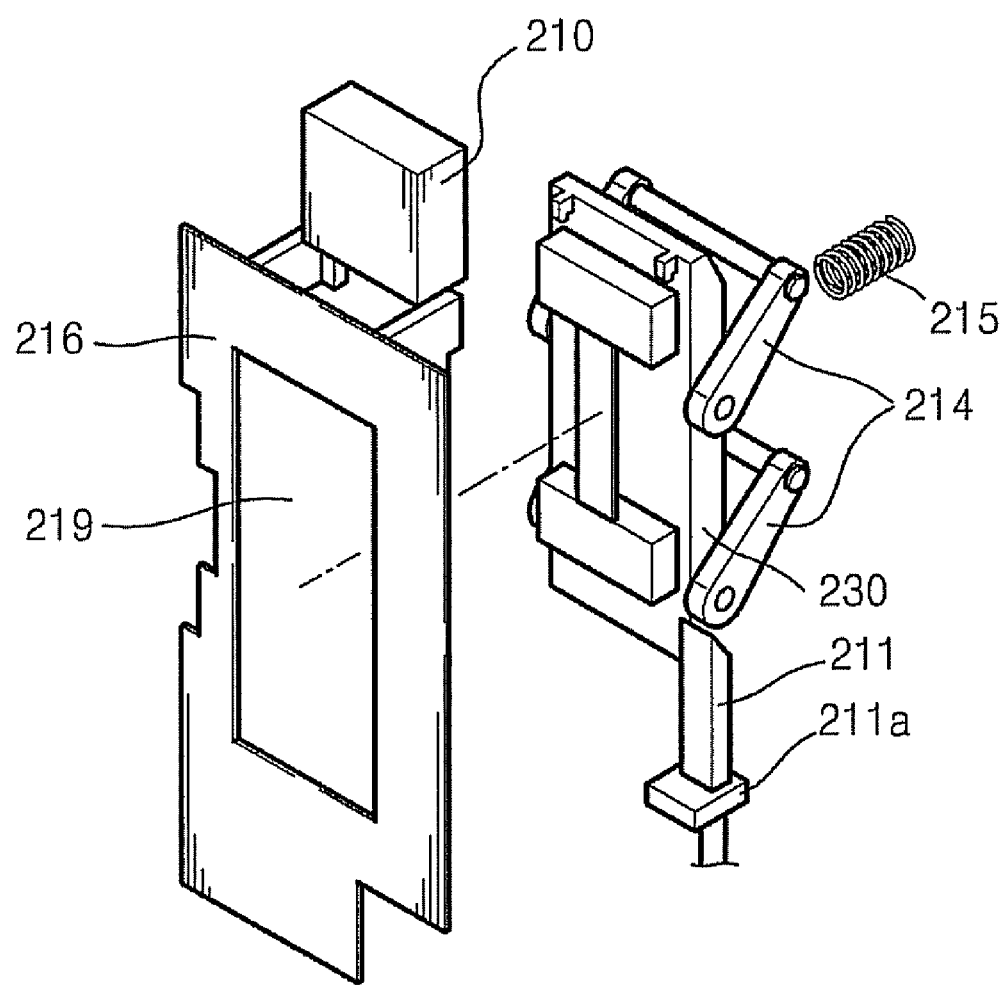

FIGS. 8A and 8B are exemplary views of the PCR chip installation unit 200 according to an embodiment of the present invention. FIG. 8A is a front perspective view of the PCR chip installation unit 200 and FIG. 8B is an exploded perspective view of the PCR chip installation unit 200. In FIG. 8A, a cover 220 is illustrated which provides a safe movement path for the PCR chip 300 when installing and/or removing the PCR chip 300 and protects the installed PCR chip 300. However, in FIG. 8B, the cover 220 is not illustrated for convenience of explanation. Referring to FIGS. 8A and 8B, the PCR chip installation unit 200 includes the cover 220, a push rod 211, an installation detecting sensor 213, a heater mounting guide 214, a chip guide 216, and the detaching button 210.

As illustrated in FIG. 8A, the cover 220 surrounds the heater unit 230 and the heater mounting guide 214. A curved protrusion corresponding to the width and height of the PCR chip 300 is formed in the center of the cover 220. Therefore, the cover 220 forms a movement path of the PCR chip 300 together with the flat chip guide 216. In other words, the PCR chip 300 is inserted between the protrusion of the cover 220 and the chip guide 216. Also, a window 225 is formed in the cover 220 so that the PCR chamber inside the PCR chip 300 can be seen when the PCR chip 300 is inserted. Therefore, the light emitted from the light source of the detecting unit 110 can be incident on the PCR solution inside the PCR chamber via the window 225, and the fluorescent light emitted from the PCR solution can also be incident on the optical system of the detecting unit 110 via the window 225.

Meanwhile, the push rod 211 locks the heater mounting guide 214 when the PCR chip 300 is not yet inserted, and when the PCR chip is inserted, releases the heater mounting guide 214. Thus, the push rod 211 applies the heater unit 230 to the PCR chip 300. A protrusion 211a is formed on the push rod 211 so that the bottom portion of the PCR chip 300 is hooked by the protrusion 211a when inserting the PCR chip 300. Therefore, the push rod 211 is pushed downwards by the PCR chip 300 when inserting the PCR chip 300, and the push rod 211 is elevated by the recovery force of a spring 212 when removing the PCR chip 300. The purpose of the installation detecting sensor 213 is to notify the operation control unit 120 of whether or not the PCR chip 300 is inserted, and can be configured in a simple switch. For example, when the switch is turned "on" by the downward motion of the push rod 211, it means that the PCR chip 300 is inserted. Conversely, when the switch is turned "off" by the upward motion of the push rod 211, it means that the PCR chip 300 is removed.

The purpose of the heater mounting guide 214 is to apply the heater unit 230 to the PCR chip 300 with an appropriate pressure. As illustrated in FIG. 8B, the heater mounting guide 214 has a link structure. That is, both ends of the heater mounting guide 214 are each rotatably coupled to the heater unit 230 and the housing 101. In such a structure, the heater mounting guide 214 is locked by the push rod 211 when the PCR chip 300 is not inserted, and when the heater mounting guide 214 is released by the downward motion of the push rod 211, the heater unit 230 is applied to the PCR chip 300 by the force of the spring 215. The purpose of the detaching button 210 is to draw back the heater mounting guide 214 so that the heater unit 230 separates from the PCR chip 300.

The operation of the PCR chip installation unit 200 will be described in detail with reference to FIGS. 9A through 9C.

Figure 9A:
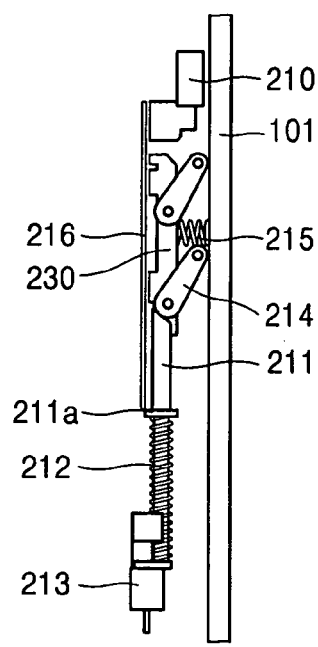
FIGS. 9A through 9C are diagrams for illustrating operations of the PCR chip installation unit illustrated in FIGS. 8A and 8B.

FIG. 9A is a side view of the PCR chip installation unit 200 when the PCR chip 300 is not inserted. The cover 220 is omitted in FIG. 9A. As illustrated in FIG. 9, the push rod 211 is elastically biased towards the heater mounting guide 214 due to the elastic force of the spring 212. Also, an end of the push rod 211 towards the heater mounting guide 214 is slanted. The slanted end of the push rod 211 pushes the heater mounting guide 214, and thus the heater unit 230 connected to the heater mounting guide 214 in the link structure is separated and drawn back from the chip guide 216.

Figure 9B:
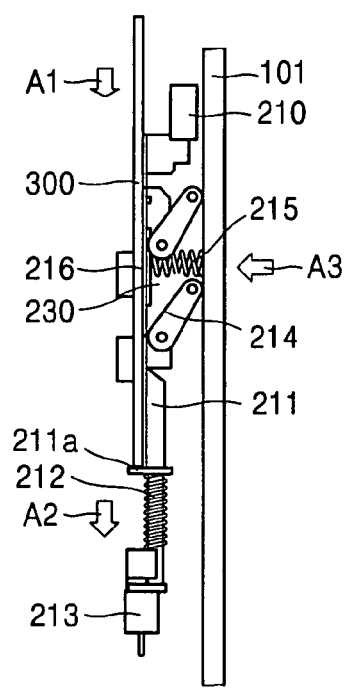

FIG. 9B is a side view of the PCR chip installation unit 200 in which the PCR chip 300 is inserted. When the PCR chip 300 is inserted between the curved protrusion (see FIG. 8A) of the cover 220 and the chip guide 216, the bottom portion of the PCR chip 300 is hooked by the protrusion 211a formed on the push rod 211, and thus the push rod 211 descends. The installation detecting sensor 213 is disposed on the bottom of the push rod 211. Therefore, when the PCR chip 300 is inserted, the switch of the installation detecting sensor 213 is pushed by the bottom portion of the push rod 211 and is turned "on," thereby notifying the operation control unit 120 that the PCR chip 300 is inserted. Meanwhile, the heater mounting guide 214 is separated from the slanted end of the push rod 211 when the push rod 211 descends. As a result, the heater unit 230 is applied to the PCR chip 300 as the heater unit 230 is pushed by the elastic force of the spring 215. That is, when the PCR chip 300 is inserted in a direction illustrated by an arrow A1, the push rod 211 moves in a direction illustrated by an arrow A2 and the heater unit 230 moves in a direction indicated by an arrow A3. An aperture 219 (see FIG. 8B) must be formed in the chip guide 216 so that the PCR chip 300 located at the front of the chip guide 216 and the heater unit 230 located at the rear of the chip guide 216 can adhere to each other.

Figure 9C:
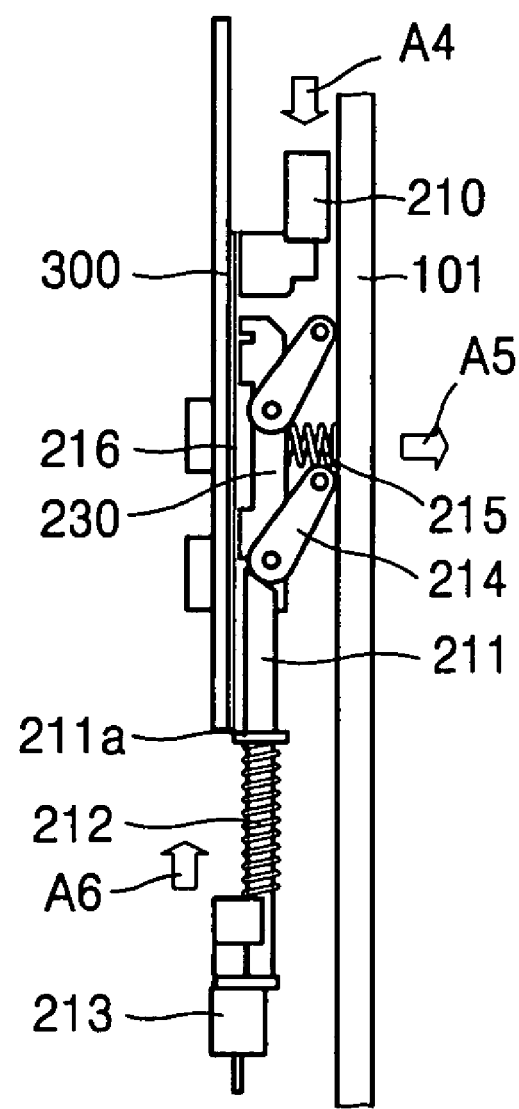

FIG. 9C is a side view of the PCR chip 300 illustrating a removal operation of the PCR chip 300. When wishing to remove the PCR chip 300, the detaching button 210 above the heater mounting guide 214 is pressed in a direction indicated by an arrow A4. Then, the heater mounting guide 214 in the link structure is pushed by the detaching button 210 and rotates. Accordingly, the heater unit 230 connected to the heater mounting guide 214 separates from the PCR chip 300 and retreats in a direction indicated by an arrow A5. Simultaneously, the push rod 211 ascends in the direction indicated by an arrow A6 due to the recovery force of the spring 212, and thus the PCR chip 300 separates from the PCR chip installation unit 200 and ascends.

Figure 10A:
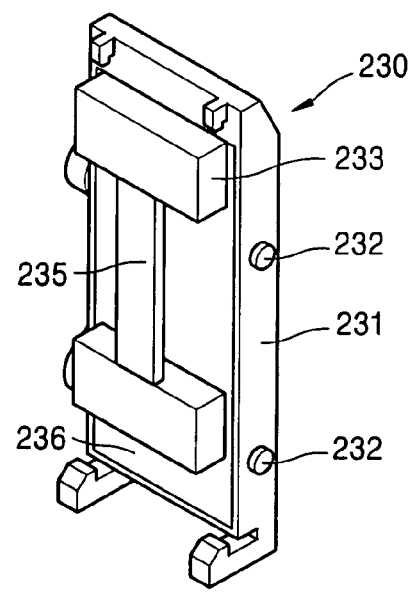
FIGS. 10A and 10B are a perspective view and a cross sectional view of a heater unit according to an embodiment of the present invention.
Figure 10B:
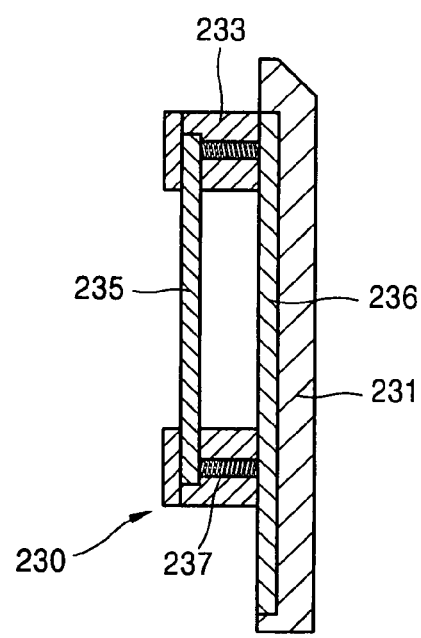

FIGS. 10A and 10B are detailed views of the heater unit 230. FIG. 10A is a perspective view of the heater unit 230 and FIG. 10B is a cross sectional view of the heater unit 230. Referring to FIGS. 10A and 10B, the heater unit 230 includes a heater plate 235 which heats the PCR chip 300 by directly contacting the PCR chip 300, a PCB substrate 236 on which a control circuit for controlling the temperature of the heater plate 235 to a preset temperature is mounted, a PCB holder 231 to which the PCB substrate 236 is fixed, and an electrode 237 vertically formed between the PCB substrate 236 and the heater plate 235 to transmit current from the PCB substrate 236 to the heater plate 235. The electrode 237 and the heater plate 235 can be fixed to each other by a heater plate guide 233 encompassing the circumference of the electrode 237 and the top of the heater plate 235. Also, the electrode 237 may prevent unstable supply of current due to poor contact caused by, for example, the vibration of the PCR module 100 by adhering the electrode 237 to the heater plate 235 using, for example, a spring. Furthermore, a contact surface of the electrode 237 and the heater plate 235 may be maximized by making the end of the electrode 237 contacting the heater plate 235 as flat as possible. Two shafts 232 are respectively formed on both sides of the PCB holder 231 so that the heater mounting guide 214 can be connected in a link structure. The heater mounting guide 214 may be rotatably coupled to the heater unit 230 via the shafts 232.

Figure 11:
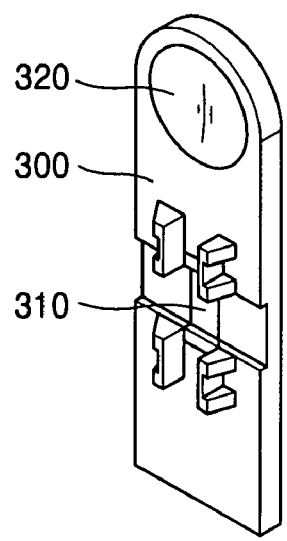
FIG. 11 is a perspective view of the structure of a PCR chip according to an embodiment of the present invention.

As described above, in the case of the prior PCR module, a user installed a PCR chip by opening a cover of the PCR module, personally placing the PCR chip on top of a heater inside the PCR module, and then closing the cover. Thus, a relatively small-sized PCR chip was manufactured since the PCR chip needs to be completely inserted into the PCR module. As a result, it is difficult for the user to handle the PCR chip, and there is a possibility of contaminating a PCR solution inside the PCR chip due to carelessness. However, in the case of the present invention, the PCR chip 300 can be installed by a one-touch operation from the outside of the PCR module 100 via the inserting slot 105 as illustrated in FIG. 5A, and thus a relatively large PCR chip 300 can be manufactured. FIG. 11 is an exemplary perspective view of the structure of the PCR chip 300. As illustrated in FIG. 11, the PCR chip 300 includes a multiple PCR chambers 310 in which a PCR reaction occurs and is formed on a substrate made of, for example, plastic, and a round handle 320 is formed at one end of the PCR chip 300 so that it is convenient for the user to handle the PCR chip 300. The user holds the PCR chip 300 by the handle 320 and vertically inserts the PCR chip 300 into the inserting slot 105 of the PCR module 100, thereby installing the PCR chip 300 in multiple PCR modules 100.

Figure 4:
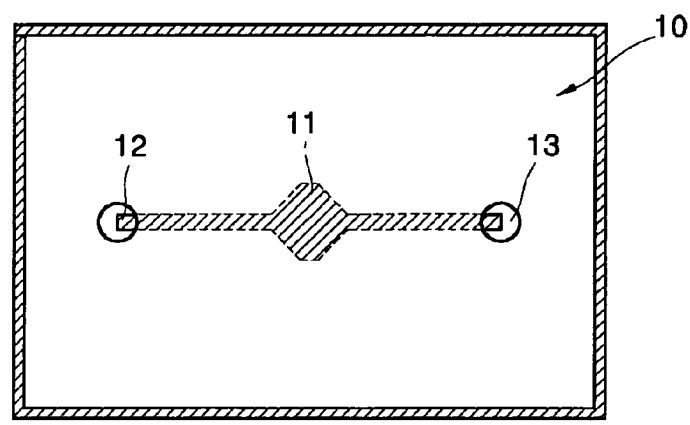
FIG. 4 is a plan view of a prior PCR chip installed in the PCR module illustrated in FIG. 3.
Figure 12:
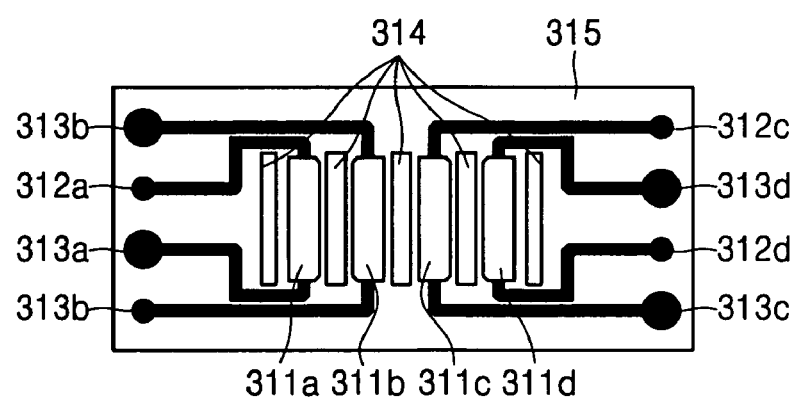
FIG. 12 is a schematic plan view of multiple PCR chambers included in the PCR chip illustrated in FIGS. 5A and 5B.

FIG. 12 is an exemplary schematic plan view of the multiple PCR chambers 310 included in the PCR chip 300. In the case of a prior PCR chip illustrated in FIG. 4, a single chamber is included in a single PCR chip. However, the PCR chip 300 according to the present invention can have a multiple chamber structure in which a plurality of chambers are included in a single PCR chip, as illustrated in FIG. 12. Therefore, it is possible to observe a PCR reaction of a number of samples at once. First through fourth chambers 311a through 311d are illustrated in FIG. 12 as an example. Referring to FIG. 12, the first through fourth chambers 311a through 311d are formed side by side on a substrate 315 made of silicon, glass, or plastic, and inlets 312a through 312d and outlets 313a through 313d are respectively connected to each of the first through fourth chambers 311a through 311d. Also, a barrier rib 314 may be further formed on both sides of each of the first through fourth chambers 311a through 311d to separate fluorescent signals generated from adjacent chambers. The fluorescent signals generated from each of the first through fourth chambers 311a through 311d are transmitted to the four optical detectors 114 via the four light transmitting elements 112 such as optical fibers illustrated in FIG. 6. A number of structures of an optical system to transmit a plurality of fluorescent signals generated from multiple chambers to optical detectors via separate light transmitting elements are disclosed. Thus, their descriptions will be omitted.

Figure 13A:
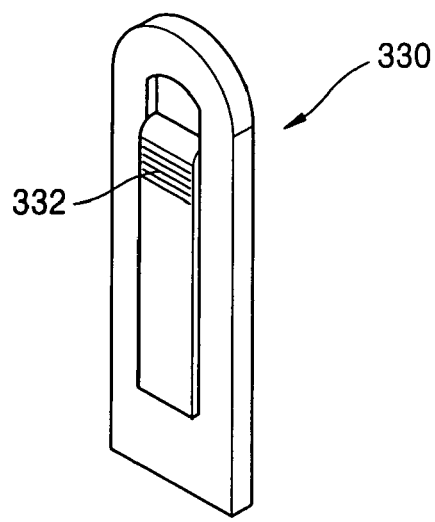
FIGS. 13A and 13B are front and rear perspective views of a heater-plate cleaning chip according to an embodiment of the present invention.
Figure 13B:
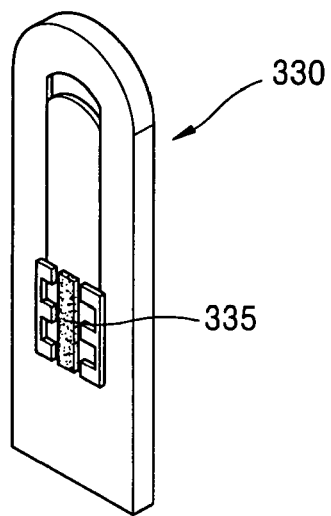

Meanwhile, in the case of the PCR module 100 of the present invention, the heater unit 230 is not exposed to the outside without dismantling the housing 101 of the PCR module 100, and thus it may be difficult to remove contamination from the heater plate 235 or to periodically clean the heater plate 235. As a result, a cleaning chip having a similar structure to the PCR chip 300 may be used to clean the heater plate 235. FIGS. 13A and 13B are front and rear perspective views of a heater-plate cleaning chip 330. As illustrated in FIGS. 13A and 13B, the heater-plate cleaning chip 330 includes a stick 332 that can move up and down mounted in a plastic substrate having a similar shape to the PCR chip 300. A top portion of the stick 332 is exposed to the outside even when the heater-plate cleaning chip 330 is completed inserted in the PCR module 100. Therefore, the user can move the stick 332 up and down by holding the top portion of the stick 332. Also, as illustrated in FIG. 13B, a cleaner 335 to clean the heater plate 235 is formed on a rear surface of the stick 332 which contacts the heater plate 235.

Figure 14:
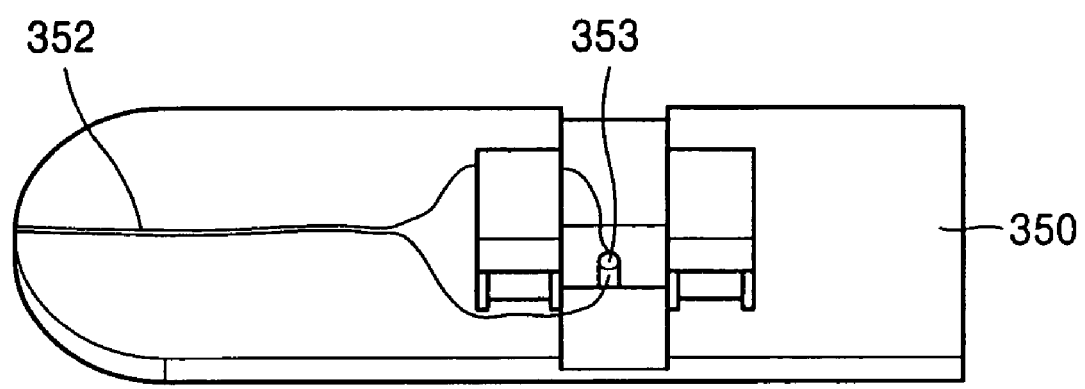
FIG. 14 is a perspective view of a temperature calibration chip of a heater unit according to an embodiment of the present invention.

In addition, in order for the optimum PCR reaction to occur, the heater unit 230 must accurately heat the PCR chip 300 with a preset temperature. Thus, the heater unit 230 should be constantly checked to determine if it is accurately operating. To do this, a temperature-adjusting chip having a similar shape to the PCR chip 300 on which a temperature sensor is formed can be produced, as in the case of the heater-plate cleaning chip 330. FIG. 14 is a perspective view of a temperature-adjusting chip 350 of the heater unit 230. As illustrated in FIG. 14, the temperature-adjusting chip 350 is structured to include a temperature sensing unit 353 in a plastic substrate having a similar shape to the PCR chip 300. A temperature sensor such as a thermocouple is mounted on a substrate made of, for example, plastic, glass, or silicon and installed in the temperature sensing unit 353. Therefore, the heater plate 235 adheres to the temperature sensing unit 353 when the temperature-adjusting chip 350 is installed in the PCR module 100. The temperature sensing unit 353 converts the temperature of the heater plate 235 into electrical signals and the electrical signals generated in the temperature sensing unit 353 are transmitted via wires 352. Thus, the temperature of the heater plate 235 can be simply measured from the outside.

Figure 2:
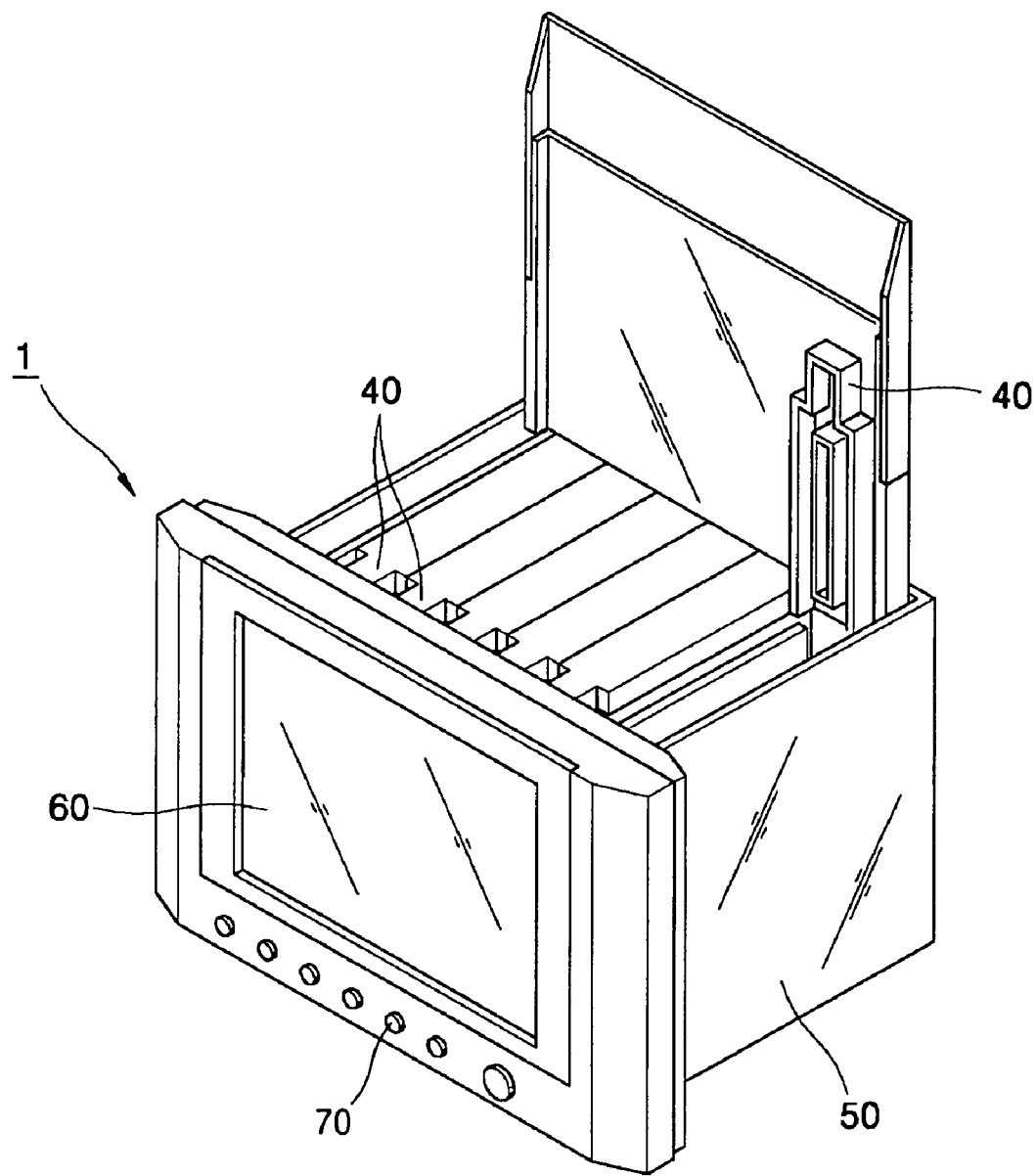
FIG. 2 is a schematic perspective view of the multiple PCR system illustrated in FIG. 1.
Figure 3:
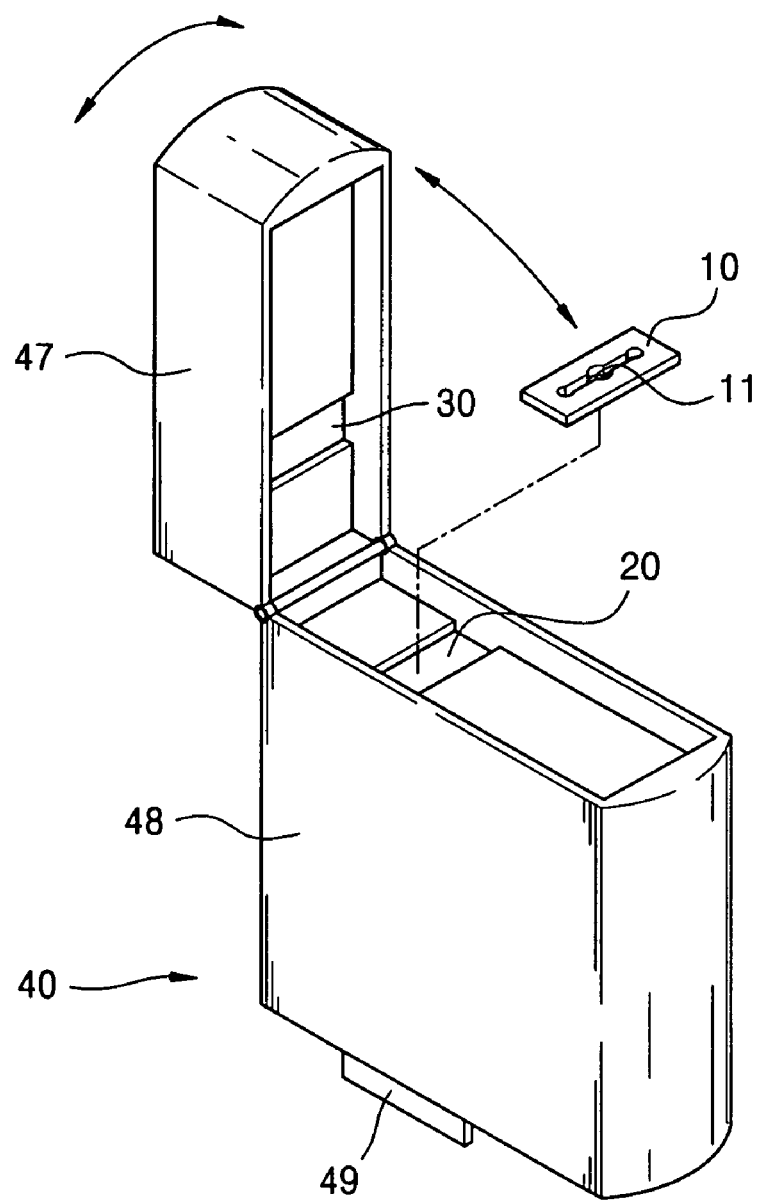
FIG. 3 is a perspective view of a prior PCR module installed in the multiple PCR system illustrated in FIG. 1.

Up to now, the structure and operation of the PCR module 100 according to an embodiment of the present invention has been explained. Any number of the above-described PCR modules 100 can be detachably installed in a PCR system illustrated in FIGS. 1 and 2 and be connected to a host computer 50 of the PCR system 1. That is, any number of PCR modules 100 can be installed in slots (not shown) in the PCR system 1 via a pin 122 protruding from each of the bottom of the PCR modules 100. Therefore, the PCR modules 100 of the present invention are installed in the PCR system 1 using the same prior method and operate in the same manner.

According to the present invention described above, a detecting unit and a heater unit installed in a PCR module are not exposed to the outside. Thus, damage to or contamination of the detecting unit or the heater unit when installing or removing a PCR chip can be prevented. In addition, according to the present invention, a user can easily install and remove the PCR chip in with one-touch, thereby making it convenient for the user to use, and there is less possibility of contaminating a PCR solution when installing the PCR chip in the PCR module due to carelessness. Furthermore, according to the present invention, a heater plate and the PCR chip are adhered to each other with optimum pressure, and thus a PCR reaction can occur at an optimum temperature.

Also, cleaning of the heater plate and adjusting the temperature of the heater plate can be performed by a simple method.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polymerase chain reaction (PCR) module, comprising:
　　a detachable PCR chip including a PCR chamber unit in which a PCR solution is accommodated;
　　a heater unit heating the PCR solution in the PCR chip with a preset temperature;
　　a detecting unit detecting unit detecting a PCR signal of the PCR solution; and
　　a PCR chip installation unit mounting and detaching the PCR chip to and from the PCR module using a one-touch method, respectively, in which the heater unit of the PCR module is adhered to the PCR chip with a predetermined pressure when mounting the PCR chip to the PCR module, and the heater unit of the PCR module is separated from the PCR chip when detaching the PCR chip from the PCR module;
　　a housing covering at least the heater unit and the detecting unit so that they are not exposed to the outside;
　　wherein the PCR chip installation unit comprises:
　　　　a heater mounting guide for adhering the heater unit to the PCR chip with the predetermined pressure when mounting the PCR chip;
　　　　a push rod which enables the PCR chip to be mounted by locking the heater mounting guide when the PCR chip is not yet mounted, and enables the heater mounting guide to adhere the heater unit to the PCR chip by releasing the heater mounting guide when mounting the PCR chip;

a detaching button to draw back the heater unit to separate the heater unit from the PCR chip when detaching the PCR chip;

a cover encompassing the heater unit and the heater mounting guide to provide a safe movement path for the PCR chip when mounting or detaching the PCR chip and to protect the PCR chip; and a flat chip guide disposed between the cover and the heater unit to form the movement path for the PCR chip together with the cover;

wherein a curved protrusion corresponding to the width and height of the PCR chip is formed in the center of the cover, and the PCR chip moves between the curved protrusion of the cover and the chip guide.

2. The PCR module of claim 1, wherein the heater mounting guide has a link structure in which respective ends of the heater mounting guide are rotatably coupled to the heater unit and the housing.

3. The PCR module of claim 2, wherein the heater unit is elastically biased towards the PCR chip by a spring.

4. The PCR module of claim 1, wherein the push rod is elastically biased towards the heater mounting guide by a spring, and a first end of the push rod pushes and locks the heater mounting guide when the PCR chip is not yet mounted.

5. The PCR module of claim 4, wherein the first end of the push rod locking the heater mounting guide is slanted, and the slanted surface pushes the heater mounting guide when the PCR chip is not yet mounted.

6. The PCR module of claim 4, wherein a protrusion is formed on a side of the push rod so that the protrusion can contact the bottom of the PCR chip when the PCR chip is being mounted.

7. The PCR module of claim 6, wherein, when mounting the PCR chip, the bottom of the PCR chip is hooked by the protrusion of the push rod and the push rod retreats from the heater mounting guide, thereby releasing the locked heater mounting guide.

8. The PCR module of claim 1, wherein the PCR chip installation unit further comprises an installation detecting sensor for detecting whether or not the PCR chip is mounted.

9. The PCR module of claim 8, wherein the installation detecting sensor is a switch that is turned "on" by being pushed by a second end of the push rod when mounting the PCR chip and is turned "off" when the PCR chip is detached.

10. The PCR module of claim 1, wherein an aperture is formed in the chip guide so that the PCR chip disposed at the front of the chip guide and the heater unit disposed at the rear of the chip guide can adhere to each other when mounting the PCR chip.

11. The PCR module of claim 1, wherein a window facing the PCR chamber unit of the PCR chip mounted inside the PCR module, is formed in a part of the cover.

12. The PCR module of claim 11, wherein light emitted from the detecting unit is incident on the PCR solution in the PCR chamber unit via the window, and fluorescent signals generated from the PCR solution are transmitted to the detecting unit via the window.

13. The PCR module of claim 1, wherein the heater unit comprises:

a heater plate for heating the PCR chip by directly contacting the PCR chip;

a substrate in which a circuit for setting a temperature of the heater plate to a preset temperature is installed;

a substrate holder for fixing the substrate; and electrodes formed between the substrate and the heater plate to transmit current from the substrate to the heater plate.

14. The PCR module of claim 13, wherein the heater unit further comprises a heater plate guide for fixing the electrodes and the heater plate together by encompassing the circumference of the electrodes and a top surface of the heater plate.

15. The PCR module of claim 14, wherein the electrodes prevent poor connection by being elastically biased towards the heater plate via a spring, and ends of the electrodes contacting the heater plate being flat.

16. The PCR module of claim 13, wherein a shaft is formed in a protrusion on both sides of the substrate holder so that the heater mounting guide can be rotatably coupled.

17. The PCR module of claim 1, wherein the PCR chip is structured to have the PCR chamber unit in which a PCR reaction can occur in a plastic substrate, and a handle is formed on an end of the PCR chip so that a user can easily hold the PCR chip.

18. The PCR module of claim 17, wherein the PCR chamber unit comprises:

a substrate made of silicon, glass, or plastic;

a plurality of chambers disposed side by side on the substrate; and inlets and outputs connected to each of the chambers.

19. The PCR module of claim 18, wherein the PCR chamber unit further comprises a plurality of barrier ribs formed on both sides of the chambers to separate fluorescent signals generated from adjacent chambers.

20. The PCR module of claim 17, further comprising a detachable heater-plate cleaning chip including:

a plastic substrate shaped the same as the substrate of the PCR chip; and a cleaner formed on a rear of the substrate to clean the heater plate.

21. The PCR module of claim 17, further comprising a detachable temperature-adjusting chip including:

a plastic substrate shaped the same as the substrate of the PCR chip; and a temperature sensing unit formed on the substrate to measure a temperature of the heater plate.

22. The PCR module of claim 1, wherein an inserting slot to mount the PCR chip is formed in the housing.

23. A PCR system comprising:

the PCR module according to claim 1; and a host computer which controls the PCR module and collects data, wherein any number of PCR modules can be detachably installed.

24. The PCR system of claim 23, wherein the PCR system simultaneously causes PCR reaction to different PCR solutions at different temperatures using multiple PCR modules in addition to monitoring multiple PCR reaction processes in real-time via the host computer.

25. The PCR system of claim 23, wherein the PCR system further comprises a plurality of slots for mounting at least one PCR module, and a pin in which electrodes are formed protrudes from a bottom of each of the PCR modules so that the PCR modules can be mounted in the slots.

* * * * *